(12) United States Patent
Sakamoto et al.

(10) Patent No.: US 6,194,219 B1
(45) Date of Patent: *Feb. 27, 2001

(54) ANALYSIS ELEMENT AND METHOD FOR PREPARING THE SAME

(75) Inventors: Hisashi Sakamoto; Yoshinori Takahashi; Yoshihiko Higuchi; Takehiro Yamaguchi, all of Kyoto (JP)

(73) Assignee: Kyoto Daiichi Kagaku Co., Ltd., Kyoto (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/713,643

(22) Filed: Sep. 13, 1996

(30) Foreign Application Priority Data

Sep. 13, 1995 (JP) .................................................... 7-273345

(51) Int. Cl.⁷ ....................................................... G01N 33/48
(52) U.S. Cl. ............................................... 436/166; 422/57
(58) Field of Search ................................. 422/56, 58, 61, 422/57; 436/166, 174, 170, 169

(56) References Cited

U.S. PATENT DOCUMENTS

| 4,868,106 | * | 9/1989 | Ito et al. ................................. 422/56 |
| 4,871,679 | * | 10/1989 | Tanaka et al. ......................... 436/79 |
| 4,966,784 | * | 10/1990 | Tanaka et al. ......................... 422/56 |
| 5,008,078 | * | 4/1991 | Yaginuma et al. .................... 422/56 |
| 5,286,624 | * | 2/1994 | Terashima et al. .................... 422/56 |

FOREIGN PATENT DOCUMENTS

| 0371513 | 6/1990 | (EP) . |
| 0481436 | 4/1992 | (EP) . |
| 2004062 | 3/1979 | (GB) . |
| 2007360 | 5/1979 | (GB) . |

* cited by examiner

*Primary Examiner*—Lyle A. Alexander
(74) *Attorney, Agent, or Firm*—Sughrue, Mion, Zinn, Macpeak & Seas, PLLC

(57) ABSTRACT

An analysis element for analyzing a specific component in a liquid sample is disclosed, which comprises a reagent comprising insoluble particles and boric acid. Furthermore, a method for preparing a reagent liquid for use in the preparation of an analysis element for analyzing a specific component in a liquid sample is disclosed, which comprises adding insoluble particles and boric acid to the reagent liquid.

16 Claims, 1 Drawing Sheet

ANALYSIS ELEMENT AND METHOD FOR PREPARING THE SAME

FIELD OF THE INVENTION

The present invention relates to an analysis element for analyzing a specific component in a liquid sample, particularly, whole blood, and a method for preparing the analysis element.

BACKGROUND OF THE INVENTION

Analysis elements for analyzing a specific component in a liquid sample are known. For example, JP-A-2-150751 (corresponding to JP-B-7-21455) discloses an analysis element comprising a support having a through-hole, a porous film to which a reagent liquid containing light-reflecting insoluble particles has been applied and dried to form a reagent layer, the porous film being fixed on the support to cover the through-hole, and a sample holding layer fixed on the support to cover the reagent layer (the terms "JP-A" and "JP-B" as used herein mean an "unexamined published Japanese patent application" and an "examined Japanese patent publication", respectively). In JP-A-2-150751, titanium oxide is used as light-reflecting insoluble particles which, when whole blood is applied to the element and observed from the support side, hide red blood cells from view and also cut off light.

Titanium dioxide particles are white particles which reflect light with little absorption and are hardly dissolved in all kinds of solvents. They have a broad particle size distribution from fine (0.001 $\mu$m) to coarse (1 mm or even greater). The smaller the particle size, the more liable to aggregation. Titanium dioxide particles are usually used in paints, ointments, cosmetics, and the like for making use of their opaqueness.

Since titanium dioxide particles are insoluble in a solvent and also liable to aggregate, they easily form lumps and precipitate in liquid, failing to provide a liquid system having a uniform concentration distribution throughout the liquid.

Therefore, in the preparation of an analysis element for analyzing a specific component in a liquid sample, a titanium dioxide dispersion (reagent liquid) undergoes aggregation and precipitation and cannot be applied to a substrate (porous film) uniformly. Such a disadvantage may be eliminated by adding a polymer or a thickener to make the reagent liquid viscous or by stirring the liquid. However, a liquid having a viscosity enough to prevent titanium dioxide particles from precipitating would have insufficient fluidity for easy application to a substrate and also deteriorate analysis precision of the analysis element. The stirring of a reagent liquid is accompanied by air entrapment. Once air bubbles are formed, they remain in the coating layer even after drying or burst to leave craters after drying.

The aggregation of titanium dioxide particles also proceed while the coating layer is being dried, making the surface of the coating layer non-uniform. When the titanium dioxide-containing layer serves as an optical reflecting layer, such non-uniformity of the surface causes non-uniform light reflection and seriously reduces the performance of the reagent layer. It has therefore been demanded to develop a technique for dispersing insoluble particles, such as titanium dioxide particles, in liquid uniformly without involving such an operation as might impair coating precision, i.e., stirring, and increasing the viscosity of the liquid more than necessary.

SUMMARY OF THE INVENTION

An object of the present invention is to provide a method for preparing a reagent liquid having stably dispersed therein insoluble particles.

Another object of the invention is to provide an analysis element comprising a reagent layer having uniformly dispersed therein insoluble particles and having a uniform thickness and an even surface.

As a result of extensive study, the inventors of the present invention have found that aggregation or precipitation of insoluble particles in liquid can be inhibited or retarded in the presence of boric acid.

That is, these and other objects of the present invention have been attained by an analysis element for analyzing a specific component in a liquid sample, which comprises a reagent comprising insoluble particles and boric acid.

Furthermore, these and other objects of the present invention have been attained by a method for preparing a reagent liquid for use in the preparation of an analysis element for analyzing a specific component in a liquid sample, which comprises adding insoluble particles and boric acid to the reagent liquid.

DETAILED DESCRIPTION OF THE INVENTION

Figure 1:
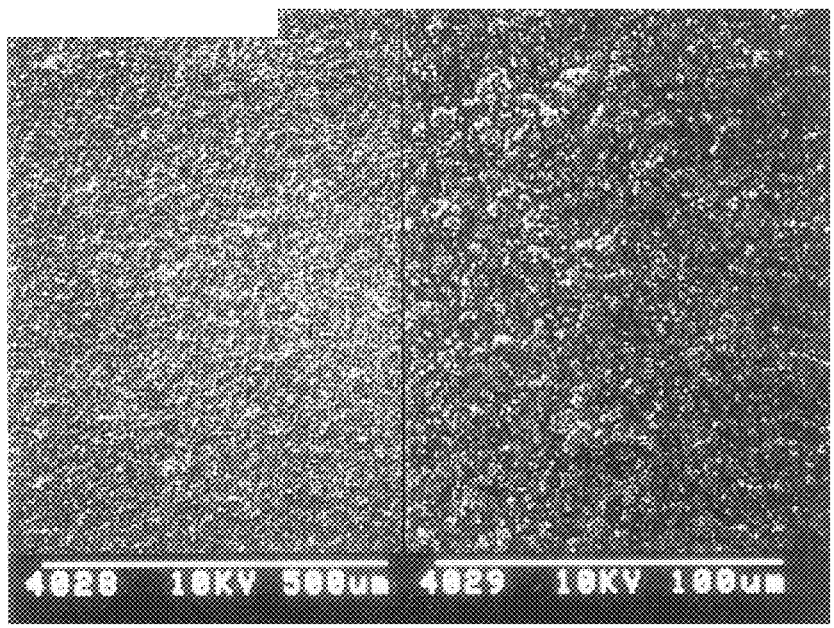
FIG. 1 shows electron micrographs taken of the surface of the analysis element prepared in Example 2 under a magnification of 100 (left-hand side) and 500 (right-hand side) by SEM (scanning electron microscope).

Insoluble particles for use in a reagent layer of an analysis element for various purposes include filter paper powders, carbon powders and light-reflecting insoluble particles. The light-reflecting insoluble particles are preferably used for hiding red blood cells and cutting off light.

Examples of the light-reflecting insoluble particles include titanium dioxide, magnesium oxide, and barium sulfate. Titanium dioxide is particularly preferred for its high whiteness.

Titanium dioxide having a general structure, such as a rutile structure or an anatase structure, or amorphous titanium dioxide is used. Rutile type titanium dioxide is preferred for its high whiteness.

The particle size of the insoluble particles is not particularly limited as long as the particles are dispersible in a reagent liquid by stirring. The present invention is particularly effective for particles having a particle size of 100 $\mu$m or smaller, preferably 0.001 to 100 $\mu$m, and more preferably 0.01 to 10 $\mu$m. The amount of the insoluble particles per the reagent liquid is preferably from 1 to 70% by weight, and more preferably from 3 to 30% by weight.

Boric acid is a chemically stable substance that does not react with a reagent and gives little influence on the sensitivity and stability of the reagent in the reagent layer. Boric acid has low water solubility, i.e., about 0.75 mol/l at 20° C., about 1.3 mol/l at 40° C., and about 2.1 mol/l at 60° C. On the other hand, boric acid is easily soluble in such a solvent as ethanol to about 1.9 mol/l at 25° C.

The boric acid is added to the reagent liquid preferably at a final concentration of 0.01 to 2 mol/l, more preferably 0.1 to 0.5 mol/l.

A preferred final concentration of boric acid in the reagent layer at the time when the liquid sample is applied for the analysis element is from 0.01 to 2 mol/l, and preferably from 0.1 to 0.5 mol/l.

Boric acid may be added to the reagent liquid either alone or in combination with sodium tetraborate to form a buffer solution or in combination with other buffer solutions. For example, boric acid may be combined with a phosphate buffer, or a boric acid buffer solution may be combined with a TES buffer.

The analysis element can be prepared by using the resulting reagent liquid in a conventional manner (e.g., the methods described in JP-B-49-33800 or JP-B-7-21455). For example, the reagent liquid is applied to a film by coating, printing or spraying and dried.

The analysis element of the present invention can be used for analyzing whole blood, serum, plasma, urine, salivary, cerebral fluid, and the like. Examples of substances measured by the analysis element include glucose, uric acid, cholesterol, urea nitrogen, bilirubin, calcium, creatinine, protein, albumin, lactate dehydrogenase (LDH), triglyceride, and amylase.

The reagent liquid of the present invention may contain analysis reagents which are usually used in a calorimetric analysis system, or binders.

Examples of the analysis reagents include oxidases (e.g., glucose oxidase, uricase, cholesterol oxidase, glycerol oxidase, bilirubin oxidase, lactate oxidase, pyruvate oxidase), peroxidase, 4-aminoantipyrine, Trinder's reagents (e.g., DAOS, TOOS, MAOS), reductases (e.g., glucose dehydrogenase, hexokinase, glucose-6-phosphate dehydrogenase), diaphorase, phenazine methosulfate, Meldola's blue, NAD, NADP, tetrazolium salts (e.g., NTB, BTB, BPB), and pH indicators (e.g., BCG, BTB, BPB).

Examples of the additives include nonionic, cationic, anionic and ampholytic surfactants, such as Triton X-100, Tween 20, and Brij 35.

The solvent for use in the reagent liquid is not particularly limited. Examples thereof include water (e.g., deionized water), methanol, ethanol, acetone, xylene, toluene, dimethylformamide, dimethylsulfoxide, methylene chloride, and cyclohexane.

Furthermore, a binder may be added to the reagent liquid. Examples thereof include hydrophilic polymers (e.g., hydroxypropyl cellulose (HPC), methyl cellulose (MC), polyvinyl alcohol (PVA), polyvinyl pyrolidone (PVP)) and hydrophobic polymers (e.g., polyvinyl butyral (PVB)).

For example, the analysis element can prepared by applying the reagent liquid to a porous film and covering a support with the reagent liquid-applied porous film. Examples of the support include a polyethylene terephthalate (PET) film, a polystyrene film, a polyethylene film, and a polycarbonate film. Examples of the porous film include a polypropylene film (e.g., Celgard™, produced by Hoechst AG), a polyethylene film (e.g., Hipore™, produced by Asahi Chemical Industry, Co., Ltd.) and a polycarbonate film (e.g., Cyclopore™, produced by Whatman).

As described above, aggregation and precipitation of insoluble particles, such as titanium dioxide, in a reagent liquid can be suppressed by incorporation of boric acid. Therefore, an insoluble particle-containing reagent liquid containing boric acid retains a stable disperse state for a sufficient time for the liquid to be applied to a substrate. Upon drying, the applied reagent liquid layer becomes a more uniform reagent layer that provides a satisfactory analysis element.

The present invention will now be illustrated in greater detail with reference to Examples, but it should be understood that the invention is not deemed to be limited thereto.

EXAMPLE 1

Into a transparent glass bottle (diameter: 2.4 cm; height: 15 cm) was put 0.75 g of titanium dioxide particles (rutile type; produced by Wako Pure Chemical Industries Co., Ltd.), and 15 ml of a liquid shown in Table 1 below was added and mixed well. The mixture was allowed to stand, and the time required for the precipitating titanium dioxide to reach the depth of 10 mm and 6 mm from the bottom of the bottle was measured. The results obtained are shown in Table 1.

TABLE 1

| Sample No. | Liquid | Time (sec) for reaching depth of: | |
|---|---|---|---|
| | | 10 mm | 6 mm |
| 1 | Distilled water | 80 | 160 |
| 2 | 0.3 mol/l Boric acid aqueous solution | 170 | 240 |
| 3 | 0.2 mol/l Phosphate buffer (pH 7.2) | 190 | 300 |
| 4 | 0.2 mol/l Phosphate buffer (pH 7.2) + 0.3 mol/l boric acid aqueous solution | 360 | 550 |
| 5 | 0.2 mol/l TES buffer (pH 7.2) | 100 | 280 |
| 6 | 0.2 mol/l TES buffer (pH 7.2) + 0.3 mol/l boric acid aqueous solution | 330 | 540 |

EXAMPLE 2

Preparation of Reagent Liquid:

| | |
|---|---|
| Glucose oxidase (produced by Toyobo Co., Ltd.) | 500 ku |
| Peroxidase (produced by Toyobo Co., Ltd.) | 300 ku |
| 4-Aminoantipyrine (produced by Kisida Kagaku Co., Ltd.) | 500 mg |
| N-Ethyl-N-(2-hydroxy-3-sulfopropyl)-3,5-dimethylaniline (produced by Dojin Kagaku Co., Ltd.) | 1 g |
| 0.15M Phosphate buffer (pH 7.0) | 10 ml |
| 0.15M Borate buffer (pH 7.0) | 90 ml |
| Propiofan (produced by BASF Japan) | 4 g |
| 50% Polyoxyethylene sorbitan monolaurate aqueous solution (produced by Nacalai Tesque Co., Ltd.) | 8 ml |
| Titanium dioxide (produced by Wako Pure Chemical Co., Ltd.) | 8 g |

The above components were mixed and stirred thoroughly to prepare a reagent liquid.

Preparation of Analysis Element:

The reagent liquid was applied to a 25 $\mu$m thick porous film (Celgard, produced by Hoechst AG) to a wet thickness of 100 $\mu$m and dried at 40° C. for 1 hour. A 7 mm×7 mm square was cut out of the coated film and stuck to a 250 $\mu$m thick polyethylene terephthalate support film having a through-hole of 4 mm in diameter so as to cover the through-hole to prepare an analysis element.

In FIG. 1 are shown electron micrographs of the coated film under a magnification of 100 (left-hand side) and 500 (right-hand side).

COMPARATIVE EXAMPLE 1

An analysis element was prepared in the same manner as in Example 2 except for using a reagent liquid having the following formulation.

| | |
|---|---|
| Glucose oxidase (produced by Toyobo Co., Ltd.) | 500 ku |
| Peroxidase (produced by Toyobo Co., Ltd.) | 300 ku |
| 4-Aminoantipyrine (produced by Kisida Kagaku Co., Ltd.) | 500 mg |
| N-Ethyl-N-(2-hydroxy-3-sulfopropyl)-3,5-dimethylaniline (produced by Dojin Kagaku Co., Ltd.) | 1 g |
| 0.15M Phosphate buffer (pH 7.0) | 100 ml |
| Propiofan (produced by BASF Japan) | 4 g |
| 50% Polyoxyethylene sorbitan monolaurate aqueous solution (produced by Nacalai Tesque Co., Ltd.) | 8 ml |
| Titanium dioxide (produced by Wako Pure Chemical Industries Co., Ltd.) | 8 g |

Figure 2:
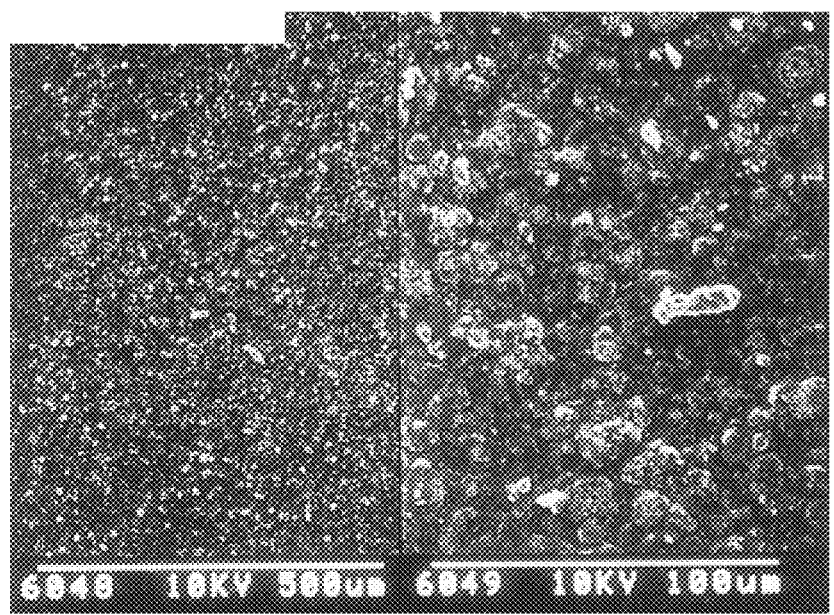
FIG. 2 shows electron micrographs taken of the surface of the analysis element prepared in Comparative Example 1 under a magnification of 100 (left-hand side) and 500 (right-hand side) by SEM.

In FIG. 2 are shown electron micrographs of the coated film under a magnification of 100 (left hand side) and 500 (right hand side).

Comparison between FIGS. 1 and 2 reveals that the reagent layer free of boric acid has coarse particles and a non-uniform surface while that containing boric acid has fine particles and a uniform surface.

Quantitative Determination of Glucose in Blood:

Whole blood (20 μl) having a varied glucose level was dropped on each of the analysis elements prepared in Example 2 and Comparative Example 1. One minute after the drop, the reflectance of the reverse side of the element (the porous film side) was measured through the through-hole of the support film with a differential calorimeter (Σ-90, manufactured by Nippon Denshoku Kogyo Co., Ltd.) at 640 nm (each n=20).

A calibration curve was prepared from the reflectances, and the measured values were converted to glucose levels based on the respective calibration curve. The results obtained are shown in Table 2 below.

In Table 2, the reproducibility is represented by a nt of variatioin (C.V) obtained by dividing a standard of 20 measured values with the average value thereof.

TABLE 2

| | Example 2 | | Compara. Example 1 | |
|---|---|---|---|---|
| Glucose level (mg/dl) | Measured value (mg/dl) | Reproducibility (C.V.) (%) | Measured value (mg/dl) | Reproducibility (C.V.) (%) |
| 110 | 111.5 | 2.3 | 115.9 | 9.5 |
| 205 | 198.7 | 1.9 | 177.1 | 13.2 |
| 489 | 485.0 | 2.8 | 398.6 | 11.8 |

As is apparent from Table 2, the analysis element according to the present invention gives satisfactory analytical results with high reproducibility on account of the uniformity of coating thickness and the surface evenness. On the other hand, the analysis element of Comparative Example 1 had poor reproducibility.

While the invention has been described in detail and with reference to specific examples thereof, it will be apparent to one skilled in the art that various changes and modifications can be made therein without departing from the spirit and scope thereof.

What is claimed is:

1. A method for preparing a reagent liquid for use in the preparation of an analysis element for analyzing a specific component in a liquid sample, which comprises adding insoluble particles and an aqueous solution consisting essentially of boric acid and water to the reagent liquid, such that when the reagent liquid is applied to a film and dried, the insoluble particles and boric acid are present in a single layer of coating on the film.

2. The method as claimed in claim 1, wherein said insoluble particles are light-reflecting.

3. The method as claimed in claim 1, wherein said insoluble particles are titanium dioxide particles, magnesium oxide particles, and barium sulfate particles.

4. The method as claimed in claim 1, wherein said insoluble particles are titanium dioxide particles.

5. The method as claimed in claim 1, wherein said insoluble particles have a particle size of 0.001 to 100 μm.

6. The method of claim 1, wherein the insoluble particles are uniformly dispersed in the single layer of coating on the film.

7. The method of claim 1, wherein said boric acid is present at a final concentration of 0.01 to 2 mol/l.

8. The method of claim 1, wherein said buffer system is a buffer solution selected from the group consisting of a phosphate buffer and a TES buffer.

9. An analysis element for analyzing a specific component in a liquid sample, which comprises a reagent liquid comprising insoluble particles and an aqueous solution consisting essentially of boric acid and water, wherein when the reagent liquid is applied to a film and dried, the insoluble particles and boric acid are present in a single layer of coating on the film.

10. The analysis element as claimed in claim 9, wherein said insoluble particles are light-reflecting.

11. The analysis element as claimed in claim 9, wherein said insoluble particles are titanium dioxide particles, magnesium oxide particles, and barium sulfate particles.

12. The analysis element as claimed in claim 9, wherein said insoluble particles are titanium dioxide particles.

13. The analysis element as claimed in claim 9, wherein said insoluble particles have a particle size of 0.001 to 100 μm.

14. The analysis element of claim 9, wherein the insoluble particles are uniformly dispersed in the single layer of coating on the film.

15. The analysis element of claim 9, wherein said boric acid is present at a final concentration of 0.01 to 2 mol/l.

16. The analysis element of claim 9, wherein said buffer system is a buffer solution selected from the group consisting of a phosphate buffer and at TES buffer.

* * * * *